United States Patent [19]

Shayman et al.

[11] Patent Number: 5,952,370
[45] Date of Patent: Sep. 14, 1999

[54] AMINO CERAMIDE-LIKE COMPOUNDS AND THERAPEUTIC METHODS OF USE

[75] Inventors: James A. Shayman; Norman S. Radin, both of Ann Arbor, Mich.

[73] Assignee: The Regents of University of Michigan, Ann Arbor, Mich.

[21] Appl. No.: 08/882,772

[22] Filed: Jun. 26, 1997

Related U.S. Application Data

[62] Division of application No. 08/708,574, Sep. 5, 1996
[60] Provisional application No. 60/004,047, Sep. 20, 1995.

[51] Int. Cl.$^6$ ...................................................... A61K 31/40
[52] U.S. Cl. ............................................................. 514/428
[58] Field of Search .................................... 514/408, 428

[56] References Cited

U.S. PATENT DOCUMENTS 5,631,394  5/1997  Wei et al. ............................... 556/404

OTHER PUBLICATIONS

Abe, A. et al., "Improved Inhibitors of Glucosylceramide Synthesis," *J. Biochem.* 111:191–196 (1992).
Abe, A. et al., "Metabolic Effects of Short–Chain Ceramide and Glucosylceramide on Sphingolipids and Protein Kinase C," *Eur. J. Biochem.* 210:765–773 (1992).
Abdel–Magid, A. et al., Metal–Assisted Aldol Condensation of Chiral A–Halogenated Imide Enolates: A Stereocontrolled Chiral Epoxide Synthesis, *J. Am. Chem. Soc.* 108:4595–4602.
Alon, R. et al., "Glycolipid Ligands for Selectins Support Leukocyte Tethering & Rolling Under Physiologic Flow Conditions." *J. Immunol.,* 154:5356–5366 (1995).
Bielawska, A. et al., "Modulation of Cell Growth and Differentiation by Ceramide," *FEBS Letters* 307:211–214 (1992).
Bielawska, A. et al., "Ceramide–Mediated Biology. Determination of Structural and Stereospecific Requirements Through the Use of N–Acyl–Phenylaminoalcohol Analogs," *J. Biol. Chem.* 267:18493–18497 (1992).
Blobe, G.C. et al., "Regulation of PKC and Its Role in Cancer Biology," *Cancer Metastasis Rev.* 13:411–431 (1994).
Brenkert, A. et al., "Synthesis of Galactosyl Ceramide and Glucosyl Ceramide by Rat Brain: Assay Procedures and Changes with Age," *Brain Res.* 36:183–193 (1972).
Carson, K.G. et al., "Studies on Morpholinosphingolipids: Potent Inhibitors of Glucosylceramide Synthase," *Tetrahedron Lett.* 35:2659–2662 (1994).
Evans, D.A. et al., "Stereoselective Aldol Condensations Via Boron Enolates," *J. Am. Chem. Soc.* 103:3099–3111 (1981).
Felding–Habermann, B. et al., "A Ceramide Analog Inhibits T Cell Proliferative Response Through Inhibition of Glycosphingolipid Synthesis and Enhancement of N,N–Dimethylsphingosine Synthesis," *Biochemistry* 29:6314–6322 (1990).

Gatt, S. et al., "Assay of Enzymes of Lipid Metabolism With Colored and Fluorescent Derivatives of Natural Lipids," *Meth. Enzymol.* 72:351–375 (1981).
Hakomori, S. "New Directions in Cancer Therapy Based on Aberrant Expression of Glycosphingolipids: Anti–adhesion and Ortho–Signaling Therapy," *Cancer Cells* 3:461–470 (1991).
Hospattankar, A.V. et al., "Changes in Liver Lipids After Administration of 2–Decanoylamino–3–Morpholinopropiophenone and Chlorpromazine," *Lipids* 17:538–543 (1982).
Inokuchi, J. et al., "Preparation of the Active Isomer of 1–Phenyl–2–Decanoylamino–3–Morpholino–1–Propanol, Inhibitor of Glucocerebroside Synthetase," *J. Lipid Res.* 28:565–571 (1987).
Inokuchi, J. et al., "Antitumor Activity in Mice of an Inhibitor of Glycosphingolipid Biosynthesis," *Cancer Lett.* 38:23–30 (1987).
Inokuchi, J. et al., "Inhibition of Experimental Metastasis of Murine Lewis Long Carcinoma by an Inhibitor of Glucosylceramide Synthase and its Possible Mechanism of Action," *Cancer Res.* 50:6731–6737 (1990).
Jaffrezou,J. et al., "Inhibition of Lysosomal Acid Sphingomyelinase by Agents which Reverse Multidrug Resistance," *Biochim. Biophys. Acta* 1266:1–8 (1995).
Kalén, A. et al., "Elevated Ceramide Levels in GH4C1 Cells Treated with Retinoic Acid," *Biochim. Biophys. Acta* 1125:90–96 (1992).
Kopaczyk, K. C. et al., "In Vivo Conversions of Cerebroside and Ceramide in Rat Brain," *J. Lipid Res.* 6:140–145 (1965).
Nakamura, K. et al., "Coomassie Brilliant Blue Staining of Lipids on Thin–Layer Plates," *Anal. Biochem.* 142:406–41 (1984).
Nicolaou, K.C. et al., "A Practical and Enantioselective Synthesis of Glycosphingolipids and Related Compounds. Total Synthesis of Globotriaosylceramide ($Gb_3$)," *J. Am. Chem. Soc.* 110:7910–7912 (1988).
Preiss, J.E. et al., "Quantitative Measurement of SN–1, 2–Diacylglycerols Present in Platelets, Hepatocytes, and Ras– and Sis–Transformed Normal Rat Kidney Cells," *J. Biol. Chem.* 261:8597–8600 (1986).

(List continued on next page.)

*Primary Examiner*—Jerome D. Goldberg
*Attorney, Agent, or Firm*—Harness, Dickey & Pierce, P.L.C.

[57] ABSTRACT

Novel amino ceramide-like compounds are provided which inhibit glucosyl ceramide (GlcCer) formation by inhibiting the enzyme GlcCer synthase, thereby lowering the level of glycosphingolipids. The compounds of the present invention have improved GlcCer synthase inhibition activity and are therefore highly useful in therapeutic methods for treating various conditions and diseases associated with altered glycosphingolipid levels.

6 Claims, 1 Drawing Sheet

OTHER PUBLICATIONS

Radin, N.S. et al., "Use of 1–Phenyl–2–Decanoylamino–3–Morpholino–1–Propanol (PDMP), and Inhibitor of Glucosylceramide Synthesis," *In NeuroProtocols, A Companion to Methods in Neurosciences,* S. K. Fisher et al., Ed., (Academic Press, San Diego) 3:145–155 (1993).

Radin, N.S. et al., "Metabolic Effects of Inhibiting Glucosylceramide Synthesis with PDMP and Other Substances," *In Advances in Lipid Research; Sphingolipids in Signaling, Part B.,* R.M. Bell et al., Ed. (Academic Press, San Diego) 28:183–213 (1993).

Radin N.S. et al., "Ultrasonic Baths as Substitutes for Shaking Incubator Baths," *Enzyme* 45:67–70 (1991).

Rosenwald, A.G. et al., "Effects of the Glycosphingolipid Synthesis Inhibitor, PDMP, on Lysosomes in Cultured Cells," *J. Lipid Res.* 35:1232 (1994).

Rosenwald, A.G. et al., "Effects of a Sphingolipid Synthesis Inhibitor on Membrane Transport Throught the Secretory Pathway," *Biochemistry* 31:3581–3590 (1992).

Shayman, J.A. et al., "Modulation of Renal Epithelial Cell Growth by Glucosylceramide: Association with Protein Kinase C, Sphingosine, and Diacylglyceride," *J. Biol. Chem.* 266:22968–22974 (1991).

Shukla, G.S. et al., "Glucosylceramide Synthase of Mouse Kidney: Further Characterization and Improved Assay Method," *Arch. Biochem. Biophys.* 283:372–378 (1990).

Shukla, A. et al., "Metabolism of D–[$^3$H]PDMP, and Inhibitor of Glucosylceramide Synthesis, and the Synergistic Action of an Inhibitor of Microsomal Monooxygenase," *J. Lipid Res.* 32:713–722 (1991).

Skehan, P. et al., "New Colorimetric Cytotoxicity Assay for Anticancer–Drug Screening," *J. Natl. Cancer Inst.* 82:1107–1112 (1990).

Strum, J.C. et al., "1–$\beta$–D–Arabinofuranosylcytosine Stimulates Ceramide and Diglyceride Formation in HL–60 Cells," *J. Biol. Chem.* 269:15493–15497 (1994).

Svensson, M. et al., "Epithelial Glucosphingolipid Expression as a Determinant of Bacterial Adherence and Cytokine Production," *Infect. and Immun.* 62:4404–4410 (1994).

Tang, W. et al., "Phorbol Ester Inhibits 13–Cis–Retinoic Acid–Induced Hydrolysis of Phosphatidylinositol 4,5–Bisphosphate in Cultured Murine Keratinocytes: a Possible Negative Feedback Via Protein Kinase C–Activation," *Cell Bioch. Funct.* 9:183–191 (1991).

Uemura, K. et al., "Effect of an Inhibitor of Glucosylceramide Synthesis on Cultured Rabbit Skin Fibroblasts," *J. Biochem. (Tokyo)* 108:525–530 (1990).

Vunnam, R.R. et al., "Analogs of Ceramide that Inhibit Glucocerebroside Synthetase in Mouse Brain," *Chem. Phys. Lipids* 26:265–278 (1980).

Zador, I.Z. et al., "A Role for Glycosphingolipid Accumulation in the Renal Hypertrophy of Streptozotocin–Induced Diabetes Mellitus," *J. Clin. Invest.* 91:797–803 (1993).

Ziche, M. et al., "Angiogenesis Can Be Stimulated or Repressed in In Vivo by a Change in GM3:GD3 Ganglioside Ration," *Lab. Invest.* 67:711–715 (1992).

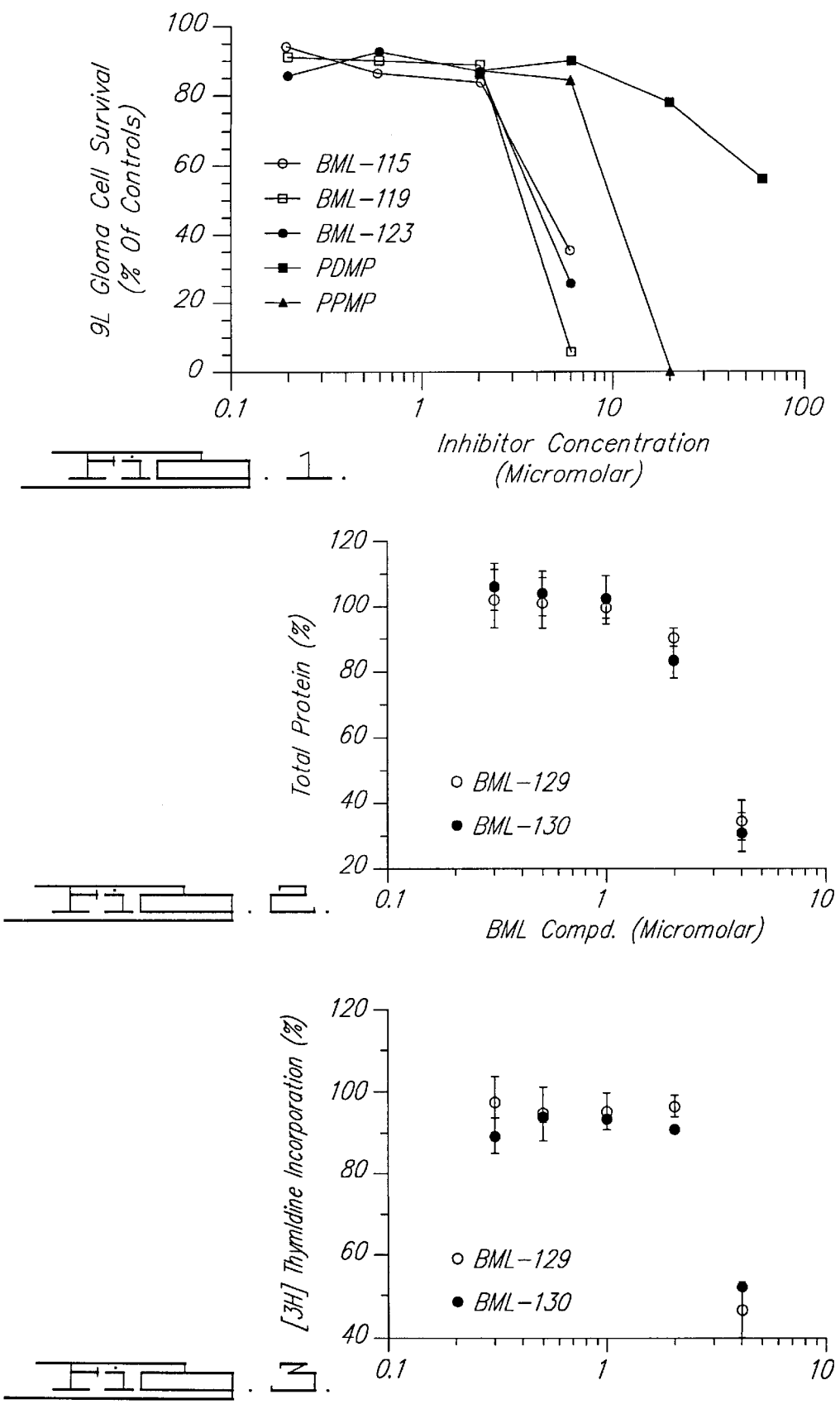

AMINO CERAMIDE-LIKE COMPOUNDS AND THERAPEUTIC METHODS OF USE

This is a division of United States patent application Ser. No. 08/708,574, filed Sep. 5, 1996, which claims priority from U.S. Ser. No. 60/004,047, filed Sep. 20, 1995.

SPONSORSHIP

The present invention was supported by Contract R43 CA 58159 from the National Cancer Institute, Grant GM 35712 from the National Institute of General Medical Sciences and by the University of Michigan Comprehensive Cancer Center grant 2P30 CA 46592 from the National Cancer Institute, U.S. Public Health Service, DHHS. The government may have certain rights in this invention.

FIELD OF THE INVENTION

The present invention relates generally to ceramide-like compounds and, more particularly, to ceramide-like compounds containing a tertiary amine group and their use in therapeutic methods.

BACKGROUND OF THE INVENTION

Hundreds of glycosphingolipids (GSLs) are derived from glucosylceramide (GlcCer), which is enzymatically formed from ceramide and UDP-glucose. The enzyme involved in GlcCer formation is UDP-glucose:N-acylsphingosine glucosyltransferase (GlcCer synthase). The rate of GlcCer formation under physiological conditions may depend on the tissue level of UDP-glucose, which in turn depends on the level of glucose in a particular tissue (Zador, I. Z. et al., "A Role for Glycosphingolipid Accumulation in the Renal Hypertrophy of Streptozotocin-Induced Diabetes Mellitus," *J. Clin. Invest.* 91:797–803 (1993)). In vitro assays based on endogenous ceramide yield lower synthetic rates than mixtures containing added ceramide, suggesting that tissue levels of ceramide are also normally rate-limiting (Brenkert, A. et al., "Synthesis of Galactosyl Ceramide and Glucosyl Ceramide by Rat Brain: Assay Procedures and Changes with Age," *Brain Res.* 36:183–193 (1972)).

It has been found that the level of GSLs controls a variety of cell functions, such as growth, differentiation, adhesion between cells or between cells and matrix proteins, binding of microorganisms and viruses to cells, and metastasis of tumor cells. In addition, the GlcCer precursor, ceramide, may cause differentiation or inhibition of cell growth (Bielawska, A. et al., "Modulation of Cell Growth and Differentiation by Ceramide," *FEBS Letters* 307:211–214 (1992)) and be involved in the functioning of vitamin $D_3$, tumor necrosis factors, interleukins, and apoptosis (programmed cell death). The sphingols (sphingoid bases), precursors of ceramide, and products of ceramide catabolism, have also been shown to influence many cell systems, possibly by inhibiting protein kinase C (PKC).

It is likely that all the GSLs undergo catabolic hydrolysis, so any blockage in the GlcCer synthase should ultimately lead to depletion of the GSLs and profound changes in the functioning of a cell or organism. An inhibitor of GlcCer synthase, PDMP (1R-phenyl-2R-decanoylamino-3-morpholino-1-propanol), previously identified as the D-threo isomer (Inokuchi, J. et al., "Preparation of the Active Isomer of 1-Phenyl-2-Decanoylamino-3-Morpholino-1-Propanol, Inhibitor of Glucocerebroside Synthetase," *J. Lipid Res.* 28:565–571 (1987)), has been found to produce a variety of chemical and physiological changes in cells and animals (Radin, N. S. et al., "Use of 1-Phenyl-2-Decanoylamino-3-Morpholino-1-Propanol (PDMP), an Inhibitor of Glucosylceramide Synthesis," *In NeuroProtocols, A Companion to Methods in Neurosciences*, S. K. Fisher et al., Ed., (Academic Press, San Diego) 3:145–155 (1993) and Radin, N. S. et al., "Metabolic Effects of Inhibiting Glucosylceramide Synthesis with PDMP and Other Substances," *In Advances in Lipid Research; Sphingolipids in Signaling, Part B.*, R. M. Bell et al., Ed. (Academic Press, San Diego) 28:183–213 (1993)). Particularly interesting is the compound's ability to cure mice of cancer induced by Ehrlich ascites carcinoma cells (Inokuchi, J. et al., "Antitumor Activity in Mice of an Inhibitor of Glycosphingolipid Biosynthesis," *Cancer Lett.* 38:23–30 (1987)), to produce accumulation of sphingosine and N,N-dimethylsphingosine (Felding-Habermann, B. et al., "A Ceramide Analog Inhibits T Cell Proliferative Response Through Inhibition of Glycosphingolipid Synthesis and Enhancement of N,N-Dimethylsphingosine Synthesis," *Biochemistry* 29:6314–6322 (1990)), and to slow cell growth (Shayman, J. A. et al., "Modulation of Renal Epithelial Cell Growth by Glucosylceramide: Association with Protein Kinase C, Sphingosine, and Diacylglyceride," *J Biol. Chem.* 266:22968–22974 (1991)). Compounds with longer chain fatty acyl groups have been found to be substantially more effective (Abe, A. et al., "Improved Inhibitors of Glucosylceramide Synthesis," *J. Biochem.* 111:191–196 (1992)).

The importance of GSL metabolism is underscored by the seriousness of disorders resulting from defects in GSL metabolizing enzymes. For example, Tay-Sachs, Gaucher's, and Fabry's diseases, resulting from enzymatic defects in the GSL degradative pathway and the accumulation of GSL in the patient, all have severe clinical manifestations. Another example of the importance of GSL function is seen in a mechanism by which blood cells, whose surfaces contain selecting, can, under certain conditions, bind to GSLs in the blood vessel walls and produce acute, life-threatening inflammation (Alon, R. et al., "Glycolipid Ligands for Selectins Support Leukocyte Tethering & Rolling Under Physiologic Flow Conditions." *J. Immunol.*, 154:5356–5366 (1995)).

At present there is only one treatment available for patients with Gaucher disease, wherein the normal enzyme which has been isolated from normal human tissues or cultured cells is administered to the patient. As with any drug isolated from human material, great care is needed to prevent contamination with a virus or other dangerous substances. Treatment for an individual patient will be extremely expensive, costing hundreds of thousands, or even millions of dollars, over a patient's lifetime. It would thus be desirable to provide a treatment which includes administration of a compound that is readily available and/or producible from common materials by simple reactions.

Possibly of even greater clinical relevance is the role of glucolipids in cancer. For example, it has been found that certain GSLs occur only in tumors; certain GSLs occur at abnormally high concentrations in tumors; certain GSLs, added to tumor cells in culture media, exert marked stimulatory or inhibitory actions on tumor growth; antibodies to certain GSLs inhibit the growth of tumors; the GSLs that are shed by tumors into the surrounding extracellular fluid inhibit the body's normal immunodefense system; the composition of a tumor's GSLs changes as the tumors become increasingly malignant; and, in certain kinds of cancer, the level of a GSL circulating in the blood gives useful information regarding the patient's response to treatment.

Because of the significant impact GSLs have on several biochemical processes, there remains a need for compounds having improved GlcCer synthase inhibition activity.

It would thus be desirable to provide compounds which inhibit GlcCer synthase activity. It would also be desirable to provide compounds which inhibit GlcCer synthase activity, thereby lowering the level of GSLs and increasing GSL precursor levels, e.g. increasing the levels of ceramide and sphingols. It would further be desirable to provide compounds which inhibit GlcCer synthase activity and lower the level of GSLs without also increasing ceramide levels. It would also be desirable to provide compounds and therapeutic methods to treat conditions and diseases associated with altered GSL levels and/or GSL precursor levels.

SUMMARY OF THE INVENTION

Novel compounds are provided which inhibit GlcCer formation by inhibiting the enzyme GlcCer synthase, thereby lowering the level of GSLs. The compounds of the present invention have improved GlcCer synthase inhibition activity and are therefore highly useful in therapeutic methods for treating various conditions and diseases associated with altered GSL levels, as well as GSL precursor levels. For example, the compounds of the present invention may be useful in methods involving cancer growth and metastasis, the growth of normal tissues, the ability of pathogenic microorganisms to bind to normal cells, the binding between similar cells, the binding of toxins to human cells, and the ability of cancer cells to block the normal process of immunological cytotoxic attack.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

FIG. 1 is a graph showing the growth and survival of 9L gliosarcoma cells grown in medium containing different GlcCer synthase inhibitors;

FIG. 2 is a graph showing the protein content of MDCK cells cultured for 24 hr in medium containing different concentrations of the separated erythro- and threo-isomers of a preferred compound of the present invention; and FIG. 3 is a graph showing [$^3$H]thymidine incorporation into the DNA of MDCK cells treated with a preferred compound of the present invention.

DETAILED DESCRIPTION OF THE PREFERRED EMBODIMENTS

Novel compounds are provided which inhibit GlcCer formation by inhibiting the enzyme GlcCer synthase, thereby lowering the level of GSLs. The compounds of the present invention have improved GlcCer synthase inhibitory activity and are therefore highly useful in therapeutic methods for treating various conditions and diseases associated with altered GSL levels.

The compounds of the present invention generally have the following formula:

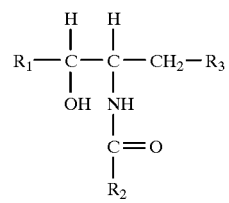

wherein $R_1$ is a phenyl group, preferably a substituted phenyl group such as p-methoxy, cyclohexyl or other acyclic group, t-butyl or other branched aliphatic group, or a long alkyl or alkenyl chain, preferably 7 to 15 carbons long with a double bond next to the kernel of the structure. The aliphatic chain can have a hydroxyl group near the two asymetric centers, corresponding to phytosphingosine.

$R_2$ is an alkyl residue of a fatty acid, 10 to 18 carbons long. The fatty acid can be saturated or unsaturated, or possess a small substitution at the C-2 position (e.g., a hydroxyl group).

$R_3$ is a tertiary amine, preferably a cyclic amine such as pyrrolidine, azetidine, morpholine or piperidine, in which the nitrogen atom is attached to the kernel (i.e., a tertiary amine).

All four structural isomers of the compounds are contemplated within the present invention and may be used either singly or in combination (i.e., DL-threo or DL-erythro).

The preferred aliphatic compound of the present invention is D-threo-1-pyrrolidino-1-deoxyceramide, identified as IV-231B herein and also referred to as PD. The preferred aromatic compound of the present invention is 1-phenyl-2-palmitoylamino-3-pyrrolidino-1-propanol, identified as BML-119 herein and also referred to as P4. The structures of the preferred compounds are as follows:

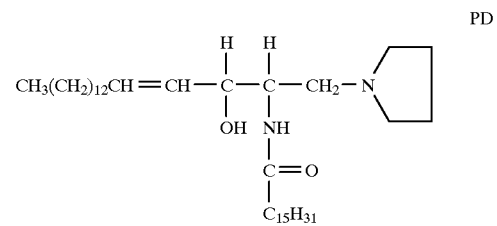

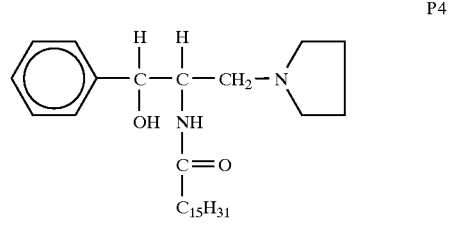

By increasing the acyl chain length of PDMP from 10 to 16 carbon atoms, the efficacy of the compounds of the present invention as GlcCer synthase inhibitors is greatly enhanced. The use of a less polar cyclic amine, especially a pyrrolidine instead of a morpholine ring, also increases the efficacy of the compounds. In addition, replacement of the phenyl ring by a chain corresponding to sphingosine yields a strongly inhibitory material. By using a chiral synthetic route, it was discovered that the isomers active against GlcCer synthase had the R,R-(D-threo)-configuration. However, strong inhibition of the growth of human cancer cells in plastico was produced by both the threo and erythro racemic compounds, showing involvement of an additional factor beyond simple depletion of cell glycosphingolipids by blockage of GlcCer synthesis. The growth arresting effects could be correlated with increases in cellular ceramide and diglyceride levels.

Surprisingly, the aliphatic pyrrolidino compound of the present invention (identified as IV-231B), was strongly inhibitory toward the GlcCer synthase and produced almost complete depletion of glycolipids, but did not inhibit growth or cause an accumulation of ceramide. Attempts were made to determine if the differences in growth effects could be attributed to the influence of the inhibitors on related enzymes (ceramide and sphingomyelin synthase and ceramidase and sphingomyelinase). While some stimulation or inhibition of enzyme activity was noted, particularly at high inhibitor concentrations (50 $\mu$M), these findings did not explain the differing effects of the different inhibitors.

By slowing the synthesis of GlcCer, the compounds of the present invention lower the levels of all the GlcCer-derived GSLs due to the GSL hydrolases which normally destroy them. While the body will continue to make the more complex GSLs from available GlcCer, the rate of synthesis will slow down as the level of GlcCer diminishes. The rate of lowering depends on the normal rate of destruction of each GSL. These rates however, are relatively rapid in animals and cultured cells.

At higher dosages, many of the compounds of the present invention produce an elevation in the level of ceramide. Presumably this occurs because cells continue to make ceramide despite their inability to utilize it for GlcCer synthesis. Ceramide is also normally converted to sphingomyelin, but this process does not seem to be able to handle the excess ceramide. It has been unexpectedly found however, that an additional process is also involved, since even those isomers that are inert against GlcCer synthase also produce an elevation in ceramide levels. Moreover, the blockage of GlcCer synthase can occur at low inhibitor dosages, yet ceramide accumulation is not produced. The preferred aliphatic compound of the present invention, D-threo-1-pyrrolidino-1-deoxyceramide (PD), does not produce ceramide accumulation at all, despite almost complete blockage of GlcCer synthesis.

This distinction between the aromatic and the aliphatic compounds of the present invention is important because ceramide has recently been proposed to cause cell death (apoptosis) by some still unknown mechanism. At lower dose levels, the aromatic compounds of the present invention cause GSL disapperance with only small accumulation of ceramide and inhibition of cell growth. Higher dosages cause much more ceramide deposition and very slow cell growth or cell death.

In one embodiment of the present invention, methods of treating patients suffering from inborn genetic errors in the metabolism of GlcCer and its normal anabolic products (lactosylceramide and the more complex GSLs) are provided. The presently known disorders in this category include Gaucher, Fabry, Tay-Sachs, Sandhoff, and GM1 gangliosidosis. The genetic errors lie in the patient's inability to synthesize a hydrolytic enzyme having normal efficiency. Their inefficient hydrolase allows the GSL to gradually accumulate to a toxic degree, debilitating or killing the victim. The compounds of the present invention slow the formation of GSLs, thus allowing the defective hydrolase to gradually "catch up" and restore the concentrations of GSLs to their normal levels and thus the compounds may be administered to treat such patients.

With respect to Gaucher disease, it has been calculated that much of the patient's accumulated GlcCer in liver and spleen arises from the blood cells, which are ultimately destroyed in these organs after they have reached the end of their life span. The actual fraction, lipid derived from blood cells versus lipid formed in the liver and spleen cells, is actually quite uncertain, but the external source must be important. Therefore it is necessary for the compounds of the present invention to deplete the blood cells as they are formed or (in the case of white blood cells) while they still circulate in the blood. Judging from toxicity tests, the white cells continue to function adequately despite their loss of GSLs. Although the toxicity studies were not of a long enough duration to produce many new red cells with low GSL content, it is possible that circulating red cells also undergo turnover (continual loss plus replacement) of GSLs.

In an alternative embodiment of the present invention, for the treatment of disorders involving cell growth and division, high dosages of the compounds of the present invention are administered but only for a relatively short time. These disorders include cancer, collagen vascular diseases, atherosclerosis, and the renal hypertrophy of diabetic patients. Accumulation or changes in the cellular levels of GSLs have been implicated in these disorders and blocking GSL biosynthesis would allow the normal restorative mechanisms of the body to resolve the imbalance.

With atherosclerosis, it has been shown that arterial epithelial cells grow faster in the presence of a GlcCer product (lactosylceramide). Oxidized serum lipoprotein, a material that normally circulates in the blood, stimulates the formation of plaques and lactosylceramide in the inner lining of blood vessels. Treatment with the compounds of the present invention would inhibit this mitogenic effect.

In an additional embodiment of the present invention, patients suffering from infections may be treated with the compounds of the present invention. Many types of pathogenic bacteria have to bind to specific GSLs before they can induce their toxic effects. As shown in Svensson, M. et al., "Epithelial Glucosphingolipid Expression as a Determinant of Bacterial Adherence and Cytokine Production," Infect. and Immun. 62:44044410 (1994), expressly incorporated by reference, PDMP treatment reduces the adherence of E. coli to mammalian cells. Several viruses, such as influenza type A, also must bind to a GSL. Several bacterial toxins, such as the verotoxins, cannot themselves act without first binding to a GSL. Thus, by lowering the level of GSLs, the degree of infection may be ameliorated. In addition, when a patient is already infected to a recognizable, diagnosable degree, the compounds of the present invention may slow the further development of the infection by eliminating the binding sites that remain free.

It has been shown that tumors produce substances, namely gangliosides, a family of GSLs, that prevent the host i.e., patient, from generating antibodies against the tumor. By blocking the tumor's ability to secrete these substances, antibodies against the tumor can be produced. Thus, by administering the GlcCer synthase inhibitors of the present invention to the patient, the tumors will become depleted of their GSLs and the body's normal immunological defenses will come into action and destroy the tumor. This technique was described in Inokuchi, J. et al., "Antitumor Activity in Mice of an Inhibitor of Glycosphingolipid Biosynthesis," Cancer Lett. 38:23–30(1987), expressly incorporated by reference. The compounds of the present invention and in particular the aliphatic compounds require much lower doses than those previously described. This is particularly important because the lower dose may reduce certain side effects. Moreover, because the aliphatic compounds of the present invention do not produce ceramide accumulation, they are less toxic. In addition, 1-phenyl-2-palmitoylamino-3-pyrrolidino-1-propanol (P4), may act via two pathways, GSL depletion and ceramide accumulation.

In an alternative embodiment, a vaccine-like preparation is provided. Here, cancer cells are removed from the patient (preferably as completely as possible), and the cells are grown in culture in order to obtain a large number of the cancer cells. The cells are then exposed to the inhibitor for a time sufficient to deplete the cells of their GLSs (generally 1 to 5 days) and are reinjected into the patient. These reinjected cells act like antigens and are destroyed by the patient's immunodefense system. The remaining cancer cells (which could not be physically removed) will also be attacked by the patient's antibodies. In a preferred embodiment, the patients circulating gangliosides in the plasma are removed by plasmapheresis, since the circulating gangliosides would tend to block the immunodefense system.

It is believed that tumors are particularly dependent on GSL synthesis for maintenance of their growth (Hakomori, S. "New Directions in Cancer Therapy Based on Aberrant Expression of Glycosphingolipids: Anti-adhesion and Ortho-Signaling Therapy," *Cancer Cells* 3:461–470 (1991)). Accumulation of ceramide in treated tumors also slows their growth or kills them. Tumors also generate large amounts of GSLs and secrete them into the patient's body, thereby preventing the host's normal response by immunoprotective cells, which should generate antibodies against or otherwise destroy tumor cells (e.g., tumors are weakly antigenic). It has also been shown that GSL depletion blocks the metastasis of tumor cells (Inokuchi, J. et al., "Inhibition of Experimental Metastasis of Murine Lewis Long Carcinoma by an Inhibitor of Glucosylceramide Synthase and its Possible Mechanism of Action," *Cancer Res.* 50:6731–6737 (1990). Tumor angiogenesis (e.g., the production of blood capillaries) is strongly influenced by GSLs (Ziche, M. et al., "Angiogenesis Can Be Stimulated or Repressed in In Vivo by a Change in GM3:GD3 Ganglioside Ratio," *Lab. Invest.* 67:711–715 (1992)). Depleting the tumor of its GSLs should block the tumors from generating the new blood vessels they need for growth.

A further important characteristic of the compounds of the present invention is their unique ability to block the growth of multidrug resistant ("MDR") tumor cells even at much lower dosages. This was demonstrated with PDMP by Rosenwald, A. G. et al., "Effects of the Glycosphingolipid Synthesis Inhibitor, PDMP, on Lysosomes in Cultured Cells," *J. Lipid Res.* 35:1232 (1994), expressly incorporated by reference. Tumor cells that survive an initial series of therapeutic treatments often reappear some years later with new properties—they are now resistant to a second treatment schedule, even with different drugs. This change has been attributed to the appearance in the tumor of large amounts of a specific MDR protein (P-glycoprotein). It has been suggested that protein kinase C (PKC) may be involved in the action or formation of P-glycoprotein (Blobe, G. C. et al., "Regulation of PKC and Its Role in Cancer Biology," *Cancer Metastasis Rev.* 13:411–431 (1994)). However decreases in PKC have other important effects, particularly slowing of growth. It is known that PDMP does lower the cellular content of PKC (Shayman, J. A. et al., "Modulation of Renal Epithelial Cell Growth by Glucosylceramide: Association with Protein Kinase C, Sphingosine, and Diacylglyceride," *J. Biol. Chem.* 266:22968–22974 (1991)) but it is not clear why it so effectively blocks growth of MDR cells (Rosenwald, A. G. et al., "Effects of the Glycosphingolipid Synthesis Inhibitor, PDMP, On Lysosomes in Cultured Cells," *J Lipid Res.* 35:1232 (1994)). A recent report showed that several lipoidal amines that block MDR action also lower the level of the enzyme acid sphingomyelinase (Jaffrezou, J. et al., "Inhibition of Lysosomal Acid Sphingomyelinase by Agents which Reverse Multidrug Resistance," *Biochim. Biophys. Acta* 1266:18 (1995)). One of these agents was also found to increase the cellular content of sphingosine 5-fold, an effect seen with PDMP as well. One agent, chlorpromazine, behaves like the compounds of the present invention, in its ability to lower tissue levels of GlcCer (Hospattankar, A. V. et al., "Changes in Liver Lipids After Administration of 2-Decanoylamino-3-Morpholinopropiophenone and Chlorpromazine," *Lipids* 17:538–543 (1982)).

It will be appreciated by those skilled in the art that the compounds of the present invention can be employed in a wide variety of pharmaceutical forms; the compound can be employed neat or admixed with a pharmaceutically acceptable carrier or other excipients or additives. Generally speaking, the compound will be administered orally or intravenously. It will be appreciated that therapeutically acceptable salts of the compounds of the present invention may also be employed. The selection of dosage, rate/frequency and means of administration is well within the skill of the artisan and may be left to the judgment of the treating physician or attending veterinarian. The method of the present invention may be employed alone or in conjunction with other therapeutic regimens. It will also be appreciated that the compounds of the present invention are also useful as a research tool e.g., to further investigate GSL metabolism.

The following Specific Example further describes the compounds and methods of the present invention.

SPECIFIC EXAMPLE

The following formulas set forth preferred aromatic and aliphatic compounds:

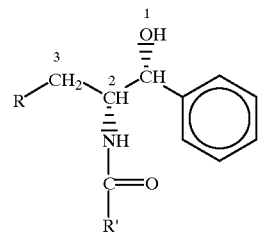

FORMULA I identified as (1R,2R)-1-phenyl-2-acylamino-3-cyclic amino-1-propanol, and referred to herein as the "aromatic inhibitors," wherein The phenyl group can be a substituted phenyl group (such as p-methoxyphenyl).

R' is an alkyl residue of a fatty acid, 10 to 18 carbons long. The fatty acid can be saturated or unsaturated, or possess a small substitution at the C-2 position (e.g., a hydroxyl group).

R is morpholino, pyrrolidino, piperidino, azetidino (trimethyleneimino), N-methylethanolamino, diethylamino or N-phenylpiperazino. A small substituent, such as a hydroxyl group, is preferably included on the cyclic amine moiety.

FORMULA II

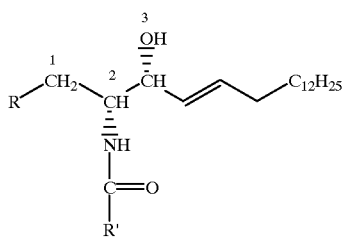

identified as (2R,3R)-2-palmitoyl-sphingosyl amine or 1-cyclic amino-1-deoxyceramide or 1-cyclic amino-2-hexadecanoylamino-3-hydroxy-octadec4,5-ene, and referred to herein as the "aliphatic inhibitors," wherein R' is an alkyl residue of a fatty acid, 10 to 18 carbons long. The fatty acid can be saturated or unsaturated, or possess a small substitution at the C-2 position (e.g., a hydroxyl group).

R is morpholino, pyrrolidino, piperidino, azetidino (trimethyleneimino), N-methylethanolamino, diethylamino or N-phenylpiperazino. A small substituent, such as a hydroxyl group, is preferably included on the cyclic amine moiety.

The long alkyl chain shown in Formula II can be 8 to 18 carbon atoms long, with or without a double bond near the asymertric carbon atom (carbon 3). Hydroxyl groups can, with advantage, be substituted along the aliphatic chain, particularly on carbon 4 (as in the naturally occurring sphingol, phytosphingosine). The long chain can also be replaced by other aliphatic groups, such at t-butyl or cyclopentyl.

The aromatic inhibitors (see Formula I and Table 1) were synthesized by the Mannich reaction from 2-N-acylaminoacetophenone, paraformaldehyde, and a secondary amine as previously described (Inokuchi, J. et al., "Preparation of the Active Isomer of 1-Phenyl-2-Decanoylamino-3-Morpholino-1-Propanol, Inhibitor of Glucocerebroside Synthetase," *J. Lipid Res.* 28:565–571 (1987) and Vunnam, R. R. et al., "Analogs of Ceramide that Inhibit Glucocerebroside Synthetase in Mouse Brain," *Chem. Phys. Lipids* 26:265–278 (1980)). For those syntheses in which phenyl-substituted starting materials were used, the methyl group in the acetophenone structure was brominated and converted to the primary amine. Bromination of p-methoxyacetophenone was performed in methanol. The acetophenones and amines were from Aldrich Chemical Co., St. Louis, Mo. Miscellaneous reagents were from Sigma Chemical Co. and the sphingolipids used as substrates or standards were prepared by methods known in the art. The reactions produce a mixture of four isomers, due to the presence of two asymmetric centers.

The aliphatic inhibitors (See Formula II and Table 2) were synthesized from the corresponding 3-t-butyldimethylsilyl-protected sphingols, prepared by enantioselective aldol condensation (Evans, D. A. et al., "Stereoselective Aldol Condensations Via Boron Enolates," *J. Am. Chem. Soc.* 103:3099–3111 (1981) and Abdel-Magid, A. et al., Metal-Assisted Aldol Condensation of Chiral A-Halogenated Imide Enolates: A Stereocontrolled Chiral Epoxide Synthesis," *J. Am. Chem. Soc.* 108:45954602 (1986)) using a modification of the procedure of Nicolaou et al. (Nicolaou, K. C. et al., "A Practical and Enantioselective Synthesis of Glycosphingolipids and Related Compounds. Total Synthesis of Globotriaosylceramide (Gb$_3$)," *J. Am. Chem. Soc.* 110:7910–7912 (1988)). Each protected sphingol was first converted to the corresponding primary triflate ester, then reacted with a cyclic amine. Subsequent N-acylation and desilylation led to the final products in good overall yield (Carson, K. G. et al., "Studies on Morpholinosphingolipids: Potent Inhibitors of Glucosylceramide Synthase," *Tetrahedron Lett.* 35:2659–2662 (1994)). The compounds can be called 1-morpholino-(or pyrrolidino)-1-deoxyceramides.

Labeled ceramide, decanoyl sphingosine, was prepared by reaction of the acid chloride and sphingosine (Kopaczyk, K. C. et al., "In Vivo Conversions of Cerebroside and Ceramide in Rat Brain," *J. Lipid Res.* 6:140–145 (1965)) and NBD-SM (12-[N-methyl-N-(7-nitrobenz-2-oxa-1,3-diazol-4-yl)]-sphingosylphosphorylcholine) was from Molecular Probes, Inc., Eugene, Oreg.

Methods

TLC of the amines was carried out with HPTLC plates (E. Merck silica gel 60) and C-M-HOAc 90:10:10 (solvent A) or 85:15:10 (solvent B) or C-M-conc. ammonium hydroxide 30:10:1 (solvent C). The bands were stained with iodine or with Coomassie Brilliant Blue R-250 (Nakamura, K. et al., "Coomassie Brilliant Blue Staining of Lipids on Thin-Layer Plates," *Anal. Biochem.* 142:40641 (1984)) and, in the latter case, quantified with a Bio-Rad Model 620 videodensitometer operated with reflected white light. The faster band of each PDMP analog, previously identified as the erythro form, corresponds to the 1S,2R and 1R,2S stereoisomers, and the slower band, previously identified as the threo form, corresponds to the 1R,2R and 1S,2S stereoisomers.

TLC of the cell lipids was run with C-M-W 24:7:1 (solvent D) or 60:35:8 (solvent E).

Growth of cell lines. Comparisons of different inhibitors with regard to suppression of human cancer cell growth were made by the University of Michigan Cancer Center in vitro Drug Evaluation Core Laboratory. MCF-7 breast carcinoma cells, HT-29 colon adenocarcinoma cells, H460 lung large cell carcinoma cells, and 9L brain gliosarcoma cells were grown in RPMI 1640 medium with 5% fetal bovine serum, 2 mM glutamine, 50 units/ml of penicillin, 50 mg/ml of streptomycin, and 0.1 mg/ml of neomycin. UMSCC-10A head and neck squamous carcinoma cells were grown in minimal essential medium with Earle salts and the same supplements. Medium components were from Sigma Chemical Co. Cells were plated in 96-well microtiter plates (1000 cells/well for H460 and 9L cells, and 2000 cells/well for the other lines), and the test compounds were added 1 day later. The stock inhibitor solutions, 2 mM in 2 mM BSA, were diluted with different amounts of additional 2 mM BSA, then each solution was diluted 500-fold with growth medium to obtain the final concentrations indicated in the Figures and Tables.

Five days after plating the H-460 and 9L cells, or 6 days for the other lines, cell growth was evaluated by staining the adhering cells with sulforhodamine B and measuring the absorbance at 520 nm (Skehan, P. et al., "New Colorimetric Cytotoxicity Assay for Anticancer-Drug Screening," *J. Natl. Cancer Inst* 82:1107–1112 (1990)). The absorbance of the treated cultures is reported as percent of that of control cultures, to provide an estimate of the fraction of the cells that survived, or of inhibition of growth rate.

For the experiments with labeled thymidine, each 8.5 cm dish contained 500,000 Madin-Darby canine kidney (MDCK) cells in 8 ml of Dulbecco modified essential supplemented medium. The cells were incubated at 37° C. in 5% $CO_2$ for 24 h, then incubated another 24 h with medium containing the inhibitor-BSA complex. The control cells were also incubated in the presence of BSA. The cells were washed with phosphatelsaline and trichloroacetic acid, then scraped off the dishes, dissolved in alkali, and analyzed for protein and DNA incorporated tritium. [Methyl-$^3$H] thymidine (10 $\mu$Ci) was added 4 h prior to harvesting.

Assay of sphingolipid enzymes. The inhibitors were evaluated for their effectiveness against the GlcCer synthase of MDCK cell homogenates by incubation in a thermostatted ultrasonic bath (Radin N. S. et al., "Ultrasonic Baths as Substitutes for Shaking Incubator Baths," Enzyme 45:67–70 (1991)) with octanoyl sphingosine and uridinediphospho [$^3$H]glucose (Shukla, G. S. et al., "Glucosylceramide Synthase of Mouse Kidney: Further Characterization and Improved Assay Method," Arch. Biochem. Biophys. 283:372–378 (1990)). The lipoidal substrate (85 $\mu$g) was added in liposomes made from 0.57 mg dioleoylphosphatidylcholine and 0.1 mg of Na sulfatide. Confluent cells were washed, then homogenized with a micro-tip sonicator at 0° C. for 3×30 sec; ~0.2 mg of protein was used in each assay tube. In the case of the aromatic inhibitors, the test compound was simply evaporated to dryness from solution in the incubation tube. This method of adding the inhibitor was found to give the same results as addition as a part of the substrate liposomes. The aliphatic inhibitors, which appeared to be less soluble in water, were added as part of the substrate liposomes.

Acid and neutral ceramidases were assayed under conditions like those above, but the medium contained 110 $\mu$M [1-$^{14}$C]decanoyl sphingosine (105 cpm) in 340 $\mu$M dioleoylphosphatidylcholine liposomes and 0.34 mg of MDCK cellular protein homogenate. The acid enzyme was incubated in 32.5 mM citrate-Na$^+$(pH 4.5) and the neutral enzyme buffer was 40 mM Tris-Cl$^-$ (pH 7.1 at 37° C.). After 60 min in the ultrasonic bath, 3 ml of C-M 2:1, carrier decanoic acid, and 0.6 ml of 0.9% saline were added and the lipids in the lower layer were separated by TLC with C-HOAc 9:1. The liberated decanoic acid was scraped off the glass plate and counted.

Ceramide synthase was assayed with 1 $\mu$M [3-$^3$H] sphingosine (70,000 cpm, repurified by column chromatography), 0.2 mM stearoyl-CoA, 0.5 mM dithiothreitol, and ~300 $\mu$g of MDCK homogenate protein in 25 mM phosphate-K$^+$ buffer, pH 7.4, in a total volume of 0.2 ml. The incubation (for 30 min) and TLC were carried out as above and the ceramide band was counted.

Sphingomyelin synthase was evaluated with 44 $\mu$M[$^{14}$C] decanoyl sphingosine (10$^5$ cpm) dispersed with 136 $\mu$M dioleoyllecithin as in the ceramide synthase assay, and 5 mM EDTA and 50 mM Hepes-Na$^+$ pH 7.5, in a total volume of 0.5 ml. MDCK homogenate was centrifuged at 600× g briefly, then at 100,000× g for 1 h, and the pellet was suspended in water and sonicated with a dipping probe. A portion of this suspension containing 300 $\mu$g of protein was used. Incubation was at 37° C. for 30 min, after which the lipids were treated as above, using C-M-W 60:35:8 for the isolation of the labeled decanoyl SM.

Acid and neutral SMase assays were based on the procedures of Gatt et al. (Gatt, S. et al., "Assay of Enzymes of Lipid Metabolism With Colored and Fluorescent Derivatives of Natural Lipids," Meth. Enzymol. 72:351–375 (1981)), using liposomes containing NBD-SM dispersed like the labeled ceramide (10 $\mu$M substrate and 30 $\mu$M lecithin). The assay medium for the neutral enzyme also contained 50 mM Tris-Cl$^-$ (pH 7.4), 25 mM KCl, 5 mM MgCl$_2$ and 0.29 mg of MDCK cell protein in a total volume of 0.25 ml. Incubation was at 37° C. for 30 min in the ultrasonic bath, then the fluorescent product, NBD-ceramide, was isolated by partitioning the assay mixture with 0.45 ml 2-propanol, 1.5 ml heptane, and 0.2 ml water. After centrifugation, a trace of contaminating NBD-SM was removed from 0.9 ml of the upper layer by washing with 0.35 ml water. The upper layer was analyzed with a fluorometer (460 nm excitation, 515 nm emission).

Acid SMase was assayed with the same liposomes in 0.2 ml of assay mixture containing 125 mM NaOAc (pH 5.0) and 61 $\mu$g of cell protein, with 60 min of incubation at 37° C. The resultant ceramide was determined as above.

Results

Table I lists the aromatic compounds (see Formula I) synthesized and their migration rates on silica gel TLC plates. Separation of the threo- and erythro-steroisomers by TLC was generally very good, except for BML-120, -121, and -122 in the acidic solvent. In the basic solvent BML-119 and BML-122 yielded poorly resolved double bands. BML-112 was unexpectedly fast-running, especially when compared with BML-120; both are presumably dihydrochlorides.

TABLE 1

Structures of the Aromatic Inhibitors

| BML Number or Name | R Group | Phenyl Substituent | TLC hR$_f$ Value[a] |
|---|---|---|---|
| PDMP[b] | morpholino | | 34(47) |
| PPMP | morpholino | | (53) |
| 112 | N-phenylpiperazino | | 56 |
| 113 | morpholino | p-fluoro | 25 |
| 114 | diethylamino | | 25 |
| 115 | piperidino (pentamethyleneimino) | | 29 |
| 116 | hexamethyleneimino | | 34 |
| 117[b] | morpholino | p-fluoro | 41 |
| 118 | piperidino | p-fluoro | 26 |
| 119 | pyrrolidino (tetramethyleneimino) | | 20–70(44) |
| 120 | 1-methylpiperazino | | 7–62 |
| 121 | 3-dimethylaminopiperidino | | 1–30 |
| 122 | N-methylethanolamino | | 6–71 |
| 123 | azetidino (trimethyleneimino) | | 12 |
| 124 | amino | | 15 |
| 125 | morpholino | p-methoxy | 37 |
| 126 | pyrrolidino | p-methoxy | (50) |

[a]Only the reltive R$_f$ value of the faster-moving band is shown. The first value was obtained with solvent A, the second with solvent C, and the numbers in parentheses, with solvent B, in the case of BML-117, -125, and -126, a 20-cm high TLC plate was used to improve the seperation.
[b]The fatty acid chain suggested by the R' group is decanoyl, not palmitoyl.

Table 2 describes four aliphatic inhibitors (see Formula II), which can be considered to be ceramide analogs in which the C-1 hydroxyl group is replaced by a cyclic amine. It should be noted that the carbon frameworks of compounds in Tables 1 and 2 are numbered differently (see Formulas I and II), thus affecting comparisons of stereochemical configurations. The threo- and erythro-isomers separated very poorly on TLC plates. Like the aromatic inhibitors, however, the morpholine compounds ran faster than the pyrrolidine compounds. The latter are presumably more strongly adsorbed by the silica gel because they are more basic.

TABLE 2

Characterization of the Sphingosyl Inhibitors

| Number | R Group | Sphingol Structure | TLC hR$_f$ Value[a] |
|---|---|---|---|
| IV-181A | morpholino | 2R,3S | 43 |
| IV-206A | morpholino | 2R,3R | 40 |
| IV-230A | pyrrolidino | 2R,3S | 31 |
| IV-231B | pyrrolidino | 2R,3R | 31 |

[a]TLC solvent: C-M-HOAC 90:5:10. Similar but faster migrations were obtained with solvent A.

Structure-activity correlations. The results of testing the compounds in an assay system for GlcCer synthase are listed in Table 3. Each inhibition determination (±SD) shown in Table 3 was carried out in triplicate. Some of the inhibitors were tested as mixtures of DL-erythro- and DL-threo-isomers (see column 4). Only the D-threo enantiomer in each mixture was predicted to be the actual enzyme inhibitor (Inokuchi, J. et al., "Preparation of the Active Isomer of 1-Phenyl-2-Decanoylamino-3-Morpholino-1-Propanol, Inhibitor of Glucocerebroside Synthetase," J. Lipid Res. 28:565–571 (1987)); the content of this isomer was calculated by measuring the proportions of the threo- and erythro-racemic mixtures by quantitative TLC. The DL-threo contents were found to be in the range of 40 to 72%. The comparisons, in the case of the mixtures, are therefore approximate (most of the samples were not purified to remove the three less-active isomers and the observed data were not corrected for the level of the primary enantiomers). The separation of the threo- and erythro- forms is most conveniently accomplished by crystallization, but the specific conditions vary for each substance; thus only BML-119, a strong inhibitor, was seperated into its threo- and erythro- forms. BML-112 is not included in Table 3 because it had no inhibitory activity against GlcCer synthase of rabbit liver microsomes.

TABLE 3

Inhibition of Ceramide Glucosyltransferase of MDCK cell Homogenates by Different Compounds

| Inhbitor Number | % Inhibition at 80 µM | Inhibition at 5 µM | Active Isomer[h] |
|---|---|---|---|
| BML-113 | 60 ± 4.7[a] | | 29 |
| BML-114 | 31 ± 2.9[a] | | 20 |
| BML-115 | 84 ± 0.8[a] | 12.4 ± 0.7[f] | 27 |
| | 82 ± 0.3[b] | | |
| BML-116 | 28 ± 3.2[a] | | 27 |
| BML-117 | 35 ± 0.6[b] | | 36 |
| BML-118 | 62 ± 0.4[b] | 8.3 ± 1.4[f] | 32 |
| BML-119 | 94 ± 1.4[b] | 51 ± 2.3[e] | 29 |
| | 97 ± 0.1[c] | 49 ± 0.8[f] | |
| | 96 ± 0.1[d] | | |
| BML-120 | 11 ± 3.0[c] | | 26 |
| BML-121 | 11 ± 0.4[c] | | 28 |
| BML-122 | 58 ± 1.6[d] | | 26 |
| BML-123 | 86 ± 0.1[d] | 15 ± 0.8[f] | 33 |
| BML-124 | -2 ± 1.6[d] | | 15 |
| BML-125 | | 9 ± 3.0[e] | 26 |
| BML-126 | 60 ± 1.8[e] | 54 ± 0.3[f] | 34 |
| PDMP | 90 ± 0.8[a] | 16 ± 1.8[f] | 100 |
| PPMP | | 32 ± 1.8[e] | 100 |
| | | 32 ± 0.7[f] | |
| IV-181A | | 12 ± 0.2[g] | 100 |
| IV-206A | | 73 ± 1.5[g] | 100 |
| IV-230A | | 19 ± 2.1[g] | 100 |
| IV-231B | | 87 ± 0.4[g] | 100 |

[a–g]Different samples were assayed as parts of different experiments.
[h]Percent of the active D-stereoisomer in the synthesized sample, estimated by scanning the two stained bands, assuming the slower one was the (racemic) active form.

Comparison of PDMP (1R,2R-decanoate) and PPMP (1R, 2R-palmitate), when evaluated at the same time in Expt. f, shows that an increase in the chain length of the N-acyl group from 10 to 16 carbon atoms distinctly improved the inhibitory activity against GlcCer synthase, as noted before (Abe, A. et al., "Improved Inhibitors of Glucosylceramide Synthesis," J. Biochem. 111:191–196 (1992)). Accordingly, most of the other compounds were synthesized with the palmitoyl group for comparison with PPMP. The comparisons between the best inhibitors are clearer at the 5 µM level.

Replacing the oxygen in the morpholine ring of PPMP with a methylene group (BML-115) improved activity ~1.4-fold (calculated from the inhibitions at 5 µM in Expt. f and relative purities, and assuming that the percent inhibition is proportional to concentration in this region: 12.4/27×100/32=1.4). Previous comparison with mouse brain, human placenta, and human Gaucher spleen glucosyltransferase also showed that replacing the morpholino ring with the piperidino ring in a ketone analog of PDMP (1-phenyl-2-decanoylamino-3-piperidino-1-propanone) produced a much more active inhibitor (Vunnam, R. R. et al., "Analogs of Ceramide that Inhibit Glucocerebroside Synthetase in Mouse Brain," Chem. Phys. Lipids 26:265–278 (1980)).

Replacing the piperidine group with a 7-membered ring (BML-116) greatly decreased the activity, while use of a 5-membered ring (BML-119) quadrupled the effectiveness (50 vs 12.4% inhibition). A 4-membered ring (BML-123) yielded a compound about as effective as the piperidino compound. The parent amine (BML-124), its N,N-diethyl analog (BML-114), and the sterically bulky N-phenylpiperazine analog (BML-1 12) displayed little or no activity.

Replacing a hydrogen atom with a fluorine atom in the p-position of the phenyl ring decreased the inhibitory power (BML-117 vs PDMP and BML-118 vs BML-115). Substitution of the p-position with an electron-donating moiety, the methoxy group, had a similar weakening effect in the case of the morpholino compound (BML-125 vs PPMP). Comparison of the pyrrolidino compounds, which are more basic than the morpholino compounds, showed that the methoxy group enhanced the inhibitory power (BML-126 vs BML-119).

Preparations of BML-119 were separated into threo and erythro racemic mixtures by HPLC on a Waters Microbondapak C$_{18}$ column, using M-W-conc. NH$_4$OH 90:10:0.2 as the elution solvent. The material eluting earlier (but migrating more slowly on a TLC plate) was called BML-130; the later eluting material (faster by TLC) was called BML-129. Assay of GlcCer synthase with each preparation at 5 µM showed 15% inhibition by BML-129 and 79% inhibition by BML-130. TLC analysis of the two preparations revealed incomplete separation, which could explain the minor inhibition by BML-129. When the two stereoisomers were separated by preparative TLC, the difference in effectiveness was found to be somewhat higher, evidently due to the better separation by this method. Thus the slower-migrating stereoisomer accounted for all or nearly all of the inhibitory activity, as noted with PDMP (Inokuchi, J. et al., "Preparation of the Active Isomer of 1-Phenyl-2-Decanoylamino-3-Morpholino-1-Propanol, Inhibitor of Glucocerebroside Synthetase," *J. Lipid Res.* 28:565–571 (1987)).

Comparison of the two pairs of aliphatic inhibitors (bottom of Table 3) showed that the 2R,3R (D-threo) form is the primary inhibitor of glucosyltransferase. This finding is in agreement with previous identification of the active PDMP isomer as being the D-threo enantiomer. However, unlike the aromatic analog, BML-129 (2R,3S/2S,3R), there was a relatively small but significant activity in the case of the (erythro) 2R,3S stereoisomer. The erythro form of PDMP was found to inhibit cell proliferation of rabbit skin fibroblasts almost as well as R,R/S,S-PDMP but it did not act on the GSLs (Uemura, K. et al., "Effect of an Inhibitor of Glucosylceramide Synthesis on Cultured Rabbit Skin Fibroblasts," *J. Biochem.* (Tokyo) 108:525–530 (1990)). As noted with the aromatic analogs, the pyrrolidine ring was more effective than the morpholine ring (Table 3).

Comparison of the aliphatic and corresponding aromatic inhibitors can be made in the case of the optically active morpholine compounds PPMP and IV-206A, both of which have the R,R structure and the same fatty acid. Here it appears that the aliphatic compound is more effective (Table 3). However in a second comparison, at lower concentrations with the inhibitors incorporated into the substrate liposomes, the degree of inhibition was 77±0.9% with 3 $\mu$M IV-231 B and 89±0.6% with 6 $\mu$M DL-threo BML-119.

Evaluations of cultured cell growth. Exposure of five different cancer cell lines to inhibitors at different concentrations for 4 or 5 days showed that the six BML compounds most active against GlcCer synthase were very effective growth inhibitors (Table 4). The $IC_{50}$ values (rounded off to one digit in the table) ranged from 0.7 to 2.6 $\mu$M.

ferences can be expected due to differences in sensitivity of the synthase occurring in each cell type (the synthases were assayed only in MDCK cells).

Growth inhibition by each of the most active BML compounds occurred in an unusually small range of concentrations (e.g., the slopes of the cytotoxic regions are unusually steep). Similar rapid drop-offs were seen in another series of tests with 9L cells, in which BML-119 yielded 71% of the control growth with 1 $\mu$M inhibitor, but only 3% of control growth with 3 $\mu$M. Growth was 93% of control growth with 2 $\mu$M BML-130 but only 5% of controls with 3 $\mu$M inhibitor. While some clinically useful drugs also show a narrow range of effective concentrations, this is a relatively uncommon relationship.

When the erythro- and threo-stereoisomeric forms of BML-119 (-129 and -130) were compared, they were found to have similar effects on tumor cell growth (Table 4). This observation is similar to the results with PDMP isomers in fibroblasts cited above (Uemura, K. et al., "Effect of an Inhibitor of Glucosylceramide Synthesis on Cultured Rabbit Skin Fibroblasts," *J. Biochem.* (Tokyo) 108:525–530 (1990)). Since enzymes are optically active and since stereoisomers and enantiomers of drugs can differ greatly in their effect on enzymes, it is likely that BML-129 and BML-130 work on different sites of closely related metabolic steps.

FIG. 2 shows the amount of cellular protein per dish for MDCK cells cultured for 24 h in medium containing different concentrations of the separated erythro- and threo-isomers of BML-119, as percent of the incorporation by cells in standard medium. Each point shown in FIG. 2 is the average of values from three plates, with error bars corresponding to one standard deviation.

FIG. 3 shows [$^3$H]thymidine incorporation into DNA of MDCK cells incubated as in FIG. 2. The values in FIG. 3 are normalized on the basis of the protein content of the incubation dishes and compared to the incorporation by cells in standard medium.

FIGS. 2 and 3 thus provide comparison of the two stereoisomers with MDCK cells. The isomers were found to

TABLE 4

Inhibition of Tumor Cell Growth In Vitro by Various Inhibitors

| Cell Type | BML-115 | BML-118 | BML-119 | BML-123 | BML-126 | BML-129 | BML-130 |
|---|---|---|---|---|---|---|---|
| MCF-7 | 2 | 2 | 2 | 2 | 1 | 3 | 2 |
| H-460 | 2 | 2 | 1 | 1 | 1 | 2 | 3 |
| HT-29 | 2 |   | 1 | 2 | 1 | 2 | 2 |
| 9L | 2 | 2 | 1 | 2 | 2 | 2 | 2 |
| UMSCC-10A | 1 |   | 1 | 1 | 1 | 2 | 2 |

FIG. 1 shows growth and survival of 9L gliosarcoma cells grown in medium containing different GlcCer synthase inhibitors, as described above. The BML compounds were used as synthesized (mixtures of DL-threo and -erythro stereoisomers) while the PDMP and PPMP were optically resolved R,R isomers. The concentrations shown are for the mixed racemic stereoisomers, since later work (Table 4) showed that both forms were very similar in effectiveness. FIG. 1 illustrates the relatively weak effectiveness of R,R-PPMP and even weaker effectiveness of R,R-PDMP. The three new compounds, however, are much better inhibitors of GlcCer synthase and growth. These differences in growth inhibitory power correlate with their effectiveness in MDCK cell homogenates as GlcCer synthase inhibitors. Some difinhibit growth and DNA synthesis with similar effectiveness. Thus the MDCK cells behaved like the human tumor cells with regard to $IC_{50}$ and the narrow range of concentrations resulting in inhibition of protein and DNA synthesis.

Surprisingly, the aliphatic inhibitor IV-231 B exerted no inhibitory effect on MDCK cell growth when incubated at 20 $\mu$M for 1 day or 1 $\mu$M for 3 days. Tests with a longer growth period, 5 days, in 5 $\mu$M inhibitor also showed no slowing of growth. The dishes of control cells, which contained BSA as the only additive to the medium, contained 3.31±0.19 mg of protein, while the IV-231B/BSA treated cells contained 3.30±0.04 mg.

Lipid changes induced in the cells. Examination by TLC of the alkali-stable MDCK lipids after a 24 h incubation disclosed that BML-130 was more effective than BML-129 in lowering GlcCer levels, as expected from its greater effectiveness in vitro as a glucosyltransferase inhibitor. The level of GlcCer, estimated visually, was greatly lowered by 0.3 $\mu$M BML-130 or 0.5 $\mu$M BML-129. The levels of the other lipids visible on the plate (mainly sphingomyelin (SM), cholesterol, and fatty acids) were changed little or not at all. BML-129 and the GlcCer synthase inhibitor, BML-130, were readily detected by TLC at the various levels used, showing that they were taken up by the cells during the incubation period at dose-dependent rates. Lactosylceramide overlapped the inhibitor bands with solvent D but was well separated with solvent E, which brought the inhibitors well above lactosylceramide.

Ceramide accumulation was similar for both stereoisomers (data not shown). An unexpected finding is that noticeable ceramide accumulation appeared only at inhibitor concentrations that were more than enough to bring GlcCer levels to a very low point (e.g., at 2 or 4 $\mu$M). The changes in ceramide concentration were quantitated in a separate experiment by the diglyceride kinase method, which allows one to also determine diacylglycerol (DAG) concentration (Preiss, J. E. et al., "Quantitative Measurement of SN-1,2-Diacylglycerols Present in Platelets, Hepatocytes, and Ras- and Sis-Transformed Normal Rat Kidney Cells," *J. Biol. Chem.* 261:8597–8600 (1986)). The results (Table 5) are similar to the visually estimated ones: at 0.4 $\mu$M BML-129 or -130 there was little effect on ceramide content but at 4 $\mu$M inhibitor, a substantial increase was observed. (While the duplicate protein contents per incubation dish were somewhat erratic in the high-dose dishes, in which growth was slow, the changes were nevertheless large and clear.) Accumulation of ceramide had previously been observed with PDMP, at a somewhat higher level of inhibitor in the medium (Shayman, J. A. et al., "Modulation of Renal Epithelial Cell Growth by Glucosylceramide: Association with Protein Kinase C, Sphingosine, and Diacylglyceride," *J. Biol. Chem.* 266:22968–22974 (1991)). From the data for cellular protein per incubation dish, it can be seen that there was no growth inhibition at the 0.4 $\mu$M level with either compound but substantial inhibition at the 4 $\mu$M level, especially with the glucosyltransferase inhibitor, BML-130. This finding is similar to the ones made in longer incubations with human cancer cells.

TABLE 5

Effects of BML-129 and -130 on MDCK Cell Growth and the Content of Ceramide and Diacylglycerol

| Growth Medium | Protein $\mu$g/dish | Ceramide nmol/mg protein | Diglyceride nmol/mg protein |
| --- | --- | --- | --- |
| Controls | 490 | 1.04 | 4.52 |
|  | 560 | 0.96 | 5.61 |
| 0.4 $\mu$m BML-129 | 500 | 1.29 | 5.51 |
|  | 538 | 0.99 | 5.13 |
| 0.4 $\mu$m BML-130 | 544 | 0.94 | 4.73 |
|  | 538 | 0.87 | 5.65 |
| 4 $\mu$m BML-129 | 396 | 3.57 | 9.30 |
|  | 311 | 3.78 | 9.68 |
| 4 $\mu$m BML-130 | 160 | 5.41 | 11.9 |
|  | 268 | 3.34 | 8.71 |

In a separate study of ceramide levels in MDCK cells, BML-130 at various concentrations was incubated with the cells for 24 h. The ceramide concentration, measured by TLC densitometry, was 1.0 nmol/mg protein at 0.5 $\mu$M, 1.1 at 1 $\mu$M, 1.5 at 2 $\mu$M, and 3.3 at 4 $\mu$M. The results with BML-129 were virtually identical.

It is interesting that the accumulation of ceramide paralleled an accumulation of diacylglycerol (DAG), as observed before with PDMP (Shayman, J. A. et al., "Modulation of Renal Epithelial Cell Growth by Glucosylceramide: Association with Protein Kinase C, Sphingosine, and Diacylglyceride," *J. Biol. Chem.* 266:22968–22974 (1991)). DAG is ordinarily considered to be an activator of protein kinase C and thus a growth stimulator, but the low level of GlcCer in the inhibited cells may counteract the stimulatory effect. Ceramide reacts with lecithin to form SM and DAG, so it is possible that the increased level of the latter reflects enhanced synthesis of the phosphosphingolipid rather than an elevated attack on lecithin by phospholipase D. Arabinofuranosylcytosine (ara-C), an antitumor agent, also produces an elevation in the DAG and ceramide of HL-60 cells (Strum, J. C. et al., "1-$\beta$-D-Arabinofuranosylcytosine Stimulates Ceramide and Diglyceride Formation in HL-60 Cells," J. Biol. Chem. 269:15493–15497 (1994)).

TLC of MDCK cells grown in the presence of 0.02 to 1 $\mu$M IV-231 B for 3 days showed that the inhibitor indeed penetrated the cells and that there was a great depletion of GlcCer, but no ceramide accumulation. The depletion of GlcCer was evident even at the 0.1 $\mu$M level and virtually no GlcCer was visible at the 1 $\mu$M level; however the more polar GSLs were not affected as strongly. After incubation for 5 days in 5 $\mu$M inhibitor, all the GSLs were virtually undetectable. The ceramide concentrations in the control and depleted cells were very similar 13.5±1.4 vs 13.9±0.2 $\mu$g/mg protein.

The lack of ceramide accumulation in cells exposed to the aliphatic inhibitors was examined further to see if it might be due to differential actions of the different inhibitors on additional enzymes involving ceramide metabolism. For example, IV-231 B might block ceramide synthase and thus prevent accumulation despite the inability of the cells to utilize ceramide for GlcCer synthesis. However, assay of ceramide synthase in homogenized cells showed it was not significantly affected by 5 $\mu$M inhibitors (Table 6). There did appear to be moderate inhibition at the 50 $\mu$M level with PDMP and the aliphatic inhibitor.

TABLE 6

Effect of Inhibitors on Acid and Neutrual Ceramidases and Ceramide Synthase of MDCK Cells

| | Enzyme Activity (% of control) | | |
| --- | --- | --- | --- |
| Inhibitor Tested | Ceramidase pH 4.5 | Ceramidase pH 7.4 | Ceramide Synthase |
| D-threo-PDMP, 5 $\mu$M | 97 ± 4 | 116 ± 19 | 99 ± 5 |
| D-threo-PDMP, 50 $\mu$M | 133 ± 13[a] | 105 ± 11 | 66 ± 9[a] |
| BML-129, 5 $\mu$M | 108 ± 8 | 100 ± 0 | 97 ± 0 |
| BML-129, 50 $\mu$M | 171 ± 26[a] | 99 ± 2 | 102 ± 1 |
| BML-130, 5 $\mu$M | 107 ± 11 | 100 ± 15 | 108 ± 10 |
| BML-130, 50 $\mu$M | 160 ± 21[a] | 100 ± 15 | 106 ± 29 |
| IV-231B, 5 $\mu$M | 106 ± 3 | 116 ± 20 | 90 ± 8 |
| IV-231B, 50 $\mu$M | 113 ± 8 | 112 ± 3 | 71 ± 18[a] |

[a]Notable differences.

Assay of the two kinds of ceramidase (Table 6) showed that there was no effect of either the aliphatic or aromatic inhibitors at the 5 $\mu$M level, at which point cell growth is completely stopped in the case of the pyrrolidino compounds. At the 50 $\mu$M level, however, the acid enzyme was stimulated markedly by the aromatic inhibitors, particularly the two stereoisomeric forms of the pyrrolidino compound.

Sphingomyelin synthase was unaffected by PDMP or the aliphatic inhibitor but BML-129 and -130 produced appreciable inhibition at 50 μM (54% and 61%, respectively) (Table 7).

TABLE 7

Effect of Inhibitors on Acid and Neutrual Sphingomyelinases and Sphingomyelin Synthase

| | Enzyme Activity (% of control) | | |
|---|---|---|---|
| Inhibitor Tested | Sphingomyelinase pH 4.5 | Sphingomyelinase pH 7.1 | Sphingomyelinase Synthase[a] |
| D-threo-PDMP, 5 μM | 102 ± 3 | 121 ± 13 | |
| D-threo-PDMP, 50 μM | 100 ± 3 | 108 ± 8 | |
| BML-129, 5 μM | 108 ± 4 | 105 ± 11 | 84 ± 27 |
| BML-129, 50 μM | 97 ± 3 | 142 ± 11[b] | 46 ± 11[b] |
| BML-130, 5 μM | 109 ± 1 | 110 ± 7 | 87 ± 14 |
| BML-130, 50 μM | 114 ± 2 | 152 ± 14[b] | 39 ± 18[b] |
| IV-231B, 5 μM | 101 ± 7 | 131 ± 3[b] | |
| IV-231B, 50 μM | 112 ± 11 | 120 ± 3[b] | |

[a]Data for PDMP and IV-231B are not shown here as they were tested in other experiments; no effect was seen.
[b]Notable differences.

Neutral sphingomyelinase (SMase) was distinctly stimulated by the aliphatic inhibitor, IV-231B, even at 5 μM (Table 7). From this one would expect that the inhibitor would produce accumulation of ceramide, yet it did not. The two pyrrolidino compounds produced appreciable stimulation at the 50 μM level. No significant effects were obtained with acid SMase.

Discussion

The present invention shows that the nature and size of the tertiary amine on ceramide-like compounds exerts a strong influence on GlcCer synthase inhibition, a 5-membered ring being most active. It also shows that the phenyl ring used previously to simulate the trans-alkenyl chain corresponding to that of sphingosine could, with benefit, be replaced with the natural alkenyl chain.

Findings with the most active GlcCer synthase inhibitors in growth tests compare favorably with evaluations of some clinically useful chemotherapeutic agents on three of the tumor cell lines in the same Drug Evaluation Core Laboratory. The IC$_{50}$ values were 0.2 to 6 μM for cisplatin, 0.02 to 44 μM for carboplatin, 0.03 to 0.2 μM for methotrexate, 0.07 to 0.2 μM for fluorouracil, and 0.1 to 1 μM for etoposide. Unlike these agents, the compounds of the present invention yielded rather similar effects with all the cell types, including MDCK cells, and thus have wider potential chemotherapeutic utility. This uniformity of action is consistent with the idea that GSLs play a wide and consistent role in cell growth and differentiation.

An important observation from the MDCK cell study is that strong inhibition of cell growth and DNA synthesis occurred only at the same concentrations of aromatic inhibitor that produced marked ceramide accumulation. This observation supports the assertion that ceramide inhibits growth and enhances differentiation or cell death (Bielawska, A. et al., "Modulation of Cell Growth and Differentiation by Ceramide," *FEBS Letters* 307:211–214 (1992)). It also agrees with previous work with octanoyl sphingosine, a short chain ceramide that produced greatly elevated levels of natural ceramide and slowed growth (Abe, A. et al., "Metabolic Effects of Short-Chain Ceramide and Glucosylceramide on Sphingolipids and Protein Kinase C," *Eur. J. Biochem.* 210:765–773 (1992)). It is also in agreement with a finding that some synthetic, nonionic ceramide-like compounds did not inhibit GlcCer synthase even though they behave like ceramide in blocking growth (Bielawska, A. et al., "Ceramide-Mediated Biology. Determination of Structural and Stereospecific Requirements Through the Use of N-Acyl-Phenylaminoalcohol Analogs," *J. Biol. Chem.* 267:18493–18497 (1992)). Compounds tested included 20 μM D-erythro-N-myristoyl-2-amino-1-phenyl-1-propanol, its L-enantiomer, the four stereoisomers of N-acetylsphinganine, and N-acetylsphingosine. Furthermore, the lack of growth inhibition and ceramide accumulation in cells treated with the aliphatic inhibitor IV-231B is also consistent with the correlation between ceramide level and growth rate.

The accumulation of ceramide that occurred at higher levels of GlcCer synthase inhibitors could be attributed not only to blockage of ceramide utilization, but also to blockage of SM synthesis or ceramide hydrolase. This possibility is especially relevant to the R,S-, S,R-, and S,S-isomers, which seem to exert effects on sphingolipids without strongly inhibiting GlcCer synthesis. The tests with both the DL-erythro-pyrrolidino inhibitor (BML-129) and the DL-threo-pyrrolidino inhibitor (BML-130), at a level producing strong growth inhibition, showed that neither material at a low concentation inhibited the enzymes tested in vitro (Tables 6 and 7) but they did cause growth inhibition as well as accumulation of ceramide. PDMP, at relatively high concentrations (50 μM), was found to inhibit SM synthase in growing CHO cells (Rosenwald, A. G. et al., "Effects of a Sphingolipid Synthesis Inhibitor on Membrane Transport Through the Secretory Pathway," *Biochemistry* 31:3581–3590 (1992)). In the test with MDCK homogenates, it did not inhibit this synthase, in agreement with the finding that labeled palmitate incorporation into SM was stimulated by PDMP (Shayman, J. A. et al., "Modulation of Renal Epithelial Cell Growth by Glucosylceramide: Association with Protein Kinase C, Sphingosine, and Diacylglyceride," *J. Biol. Chem.* 266:22968–22974 (1991)).

Retinoic acid is a growth inhibitor of interest in cancer chemotherapy and a possible adjunct in the use of the inhibitors of the present invention. It has been found to elevate ceramide and DAG levels (Kalén, A. et al., "Elevated Ceramide Levels in GH4C1 Cells Treated with Retinoic Acid," *Biochim. Biophys. Acta* 1125:90–96 (1992)) and possibly lower lecithin content (Tang, W. et al., "Phorbol Ester Inhibits 13-Cis-Retinoic Acid-induced Hydrolysis of Phosphatidylinositol 4,5-Bisphosphate in Cultured Murine Keratinocytes: a Possible Negative Feedback Via Protein Kinase C-Activation," *Cell Bioch. Funct.* 9:183–191 (1991)).

D-threo-PDMP was found to be rather active in delaying tumor cell growth or in producing complete cures in mice (Inokuchi, J. et al., "Antitumor Activity in Mice of an Inhibitor of Glycosphingolipid Biosynthesis," *Cancer Lett.* 38:23–30 (1987)) but high doses were needed. From the data in FIG. 1, the inhibitors of the present invention are approximately 30 times as active, so the dosage levels are typical of clinically useful drugs. The need to use high doses with PDMP was attributed to rapid inactivation by cytochrome P450 (Shukla, A. et al., "Metabolism of D-[$^3$H]PDMP, an Inhibitor of Glucosylceramide Synthesis, and the Synergistic Action of an Inhibitor of Microsomal Monooxygenase," *J. Lipid Res.* 32:713–722 (1991)). Cytochrome P450 can be readily blocked by various nontoxic drugs such as cimetidine, therefore high levels of the compounds of the present invention can be maintained.

The foregoing discussion discloses and describes merely exemplary embodiments of the present invention. One skilled in the art will readily recognize from such discussion, and from the accompanying drawings, that various changes, modifications and variations can be made therein without departing from the spirit and scope of the invention.

All publications cited herein are expressly incorporated by reference.

We claim:

1. A method for decreasing excessive cell growth or cell division sensitive to the compounds below, in a mammal, comprising the step of administering to the mammal a therapeutically effective amount of a compound selected from the group consisting of compounds of the formula:

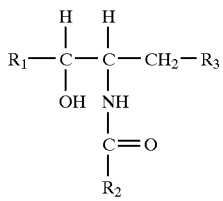

where $R_1$ is an aromatic structure, an alicyclic structure, a branched aliphatic structure or a linear aliphatic group having 5 to 15 carbons;

$R_2$ is an aliphatic chain having 9 to 18 carbons; and $R_3$ is pyrrolidino;

and functional homologues, isomers and pharmaceutically acceptable salts thereof.

2. The method of claim 1, where $R_1$ is a phenyl group.

3. The method of claim 1, where $R_1$ is p-methoxyphenyl.

4. The method of claim 1, where $R_2$ is $C_{15}H_{31}$.

5. The method of claim where the compound is 1-phenyl-2-palmitoylamino-3-pyrrolidino-1-propanol and pharmaceutically acceptable salts thereof.

6. The method of claim 1, where the cell growth or cell division is of the smooth muscle cells of the mammal's arteries.

* * * * *

UNITED STATES PATENT AND TRADEMARK OFFICE
CERTIFICATE OF CORRECTION

PATENT NO. : 5,952,370
DATED : September 14, 1999
INVENTOR(S) : Shayman et al.

Page 1 of 2

It is certified that error appears in the above-identified patent and that said Letters Patent is hereby corrected as shown below:

On the Title Page under "Other Publications," Col. 1, line 9, Information Disclosure Citation attached to Office Action dated 2-5-98, sheet 1 of 4 under "Other Documents," line 7, after "4602" insert --(1986)--.

On the Title Page under "Other Publications," Col. 2, line 14, Information Disclosure Citation attached to Office Action dated 2-5-98, sheet 2 of 4 under "Other Documents," line 19, "Synthetase" should be --Synthase--.

On page 2 of the Title Page under "Other Publications," Col. 1, line 18, Information Disclosure Citation attached to Office Action dated 2-5-98, sheet 3 of 4 under "Other Documents," line 24, "Throught" should be --Through--.

On page 2 of the Title Page under "Other Publications," Col. 2, line 26, Information Disclosure Citation attached to Office Action dated 2-5-98, sheet 4 of 4 under "Other Documents," line 22, "Ration" should be --Ratio--.

Column 1, line 52, "factors" should be --factor-$\alpha$--.
Column 1, line 66, "Synthetase" should be --Synthase--.
Column 2, line 37, "selecting" should be --selectins--.
Column 6, line 41, "44044410" should be --4404-4410--.
Column 7, line 11, "GLSs" should be --GSLs--.
Column 7, line 17, "patients" should be --patient's--.
Column 8, line 8, "1266:18" should be --1266:1-8--.
Column 9, line 15, "octadec4" should be --octadec-4--.
Column 9, line 62, "45954602" should be --4595-4602--.
Column 10, line 23, "142:40641" should be --142:406-41--.
Column 10, line 37, "H460" should be --H-460--.
Column 10, line 46, "H460" should be --H-460--.
Column 11, line 2, "phosphatelsaline" should be --phosphate/saline--.
Column 11, line 29, "105" should be --$10^5$--.
Column 12, line 50, "reltive" should be --relative--.

UNITED STATES PATENT AND TRADEMARK OFFICE
CERTIFICATE OF CORRECTION

PATENT NO. : 5,952,370
DATED : September 14, 1999
INVENTOR(S) : Shayman et al.

It is certified that error appears in the above-identified patent and that said Letters Patent is hereby corrected as shown below:

Column 13, line 11, "C-M-HOAC" should be --C-M-HoAc--.
Column 13, line 37, "seperated" should be --separated--.
Column 13, line 46, "Inhbitor" should be --Inhibitor--.
Column 14, line 6, "Inhbitor" should be --Inhibitor--.
Column 14, line 45, "(BML-1 12)" should be --(BML-112)--.
Column 18, line 28, after "similar" insert --:--.
Column 18, line 44, "Neutrual" should be --Neutral--
Column 19, line 6, "Neutrual" should be --Neutral--.
Column 22, line 14, after "claim" insert --1--.

Signed and Sealed this

Twenty-ninth Day of May, 2001

Attest:

NICHOLAS P. GODICI

*Attesting Officer*   *Acting Director of the United States Patent and Trademark Office*